(12) United States Patent
Zhu

(10) Patent No.: US 10,849,658 B2
(45) Date of Patent: Dec. 1, 2020

(54) TROCAR SEAL MEMBRANE AND ASSEMBLY COMPRISING CONCAVE-CHANNELS

(71) Applicant: 5RMED TECHNOLOGY(CHENGDU) CO., LTD., Chengdu (CN)

(72) Inventor: Moshu Zhu, Chengdu (CN)

(*) Notice: Subject to any disclaimer, the term of this patent is extended or adjusted under 35 U.S.C. 154(b) by 106 days.

(21) Appl. No.: 16/243,587

(22) Filed: Jan. 9, 2019

(65) Prior Publication Data

US 2019/0142466 A1    May 16, 2019

Related U.S. Application Data

(63) Continuation of application No. PCT/CN2017/093607, filed on Jul. 20, 2017.

(30) Foreign Application Priority Data

Aug. 2, 2016 (CN) .......................... 2016 1 0625833

(51) Int. Cl.
  *A61B 17/34* (2006.01)
  *A61M 39/06* (2006.01)
  *A61B 17/00* (2006.01)

(52) U.S. Cl.
  CPC ...... *A61B 17/3498* (2013.01); *A61B 17/3439* (2013.01); *A61B 17/3462* (2013.01); *A61M 39/06* (2013.01); *A61B 2017/00845* (2013.01); *A61B 2017/347* (2013.01); *A61B 2017/3441* (2013.01); *A61B 2017/3464* (2013.01)

(58) Field of Classification Search
  CPC .............. A61B 17/3462; A61M 39/06; A61M 2039/0626; A61M 2039/0686; A61M 2039/0633; A61M 2039/0653; A61M 2039/0673; A61M 2039/064; A61M 2039/0646; A61M 39/0606
  See application file for complete search history.

(56) References Cited

U.S. PATENT DOCUMENTS

| 5,342,315 | A | 8/1994 | Rowe et al. |
| 5,827,228 | A | 10/1998 | Rowe et al. |
| 7,112,185 | B2 | 9/2006 | Hart et al. |

(Continued)

FOREIGN PATENT DOCUMENTS

| CN | 1031587 A | 3/1989 |
| CN | 200940627 Y | 8/2007 |

(Continued)

OTHER PUBLICATIONS

Internation Search Report of PCT/CN2017/093607, dated Oct. 30, 2017.

*Primary Examiner* — Emily L Schmidt
(74) *Attorney, Agent, or Firm* — Erson IP (Nelson IP)

(57) ABSTRACT

Disclosed is a seal membrane and assembly including the concave-channel. The seal membrane includes a proximal opening, a distal aperture, and a sealing wall from the distal aperture extending to the proximal opening. The sealing wall includes a proximal surface and a distal surface. The distal aperture is formed by a sealing lip for accommodating the inserted instrument and forming a gas-tight seal. The sealing wall includes a main rotary-wall and multiple concave-channels.

6 Claims, 11 Drawing Sheets

(56) References Cited

U.S. PATENT DOCUMENTS

| | | | |
|---|---|---|---|
| 7,153,386 B2 | 12/2006 | Sagstetter | |
| 7,591,802 B2 | 9/2009 | Johnson et al. | |
| 7,842,014 B2 | 11/2010 | Schweitzer et al. | |
| 2006/0217665 A1* | 9/2006 | Prosek | A61M 39/0606 |
| | | | 604/167.02 |
| 2006/0252019 A1 | 11/2006 | Burkitt | |
| 2007/0255218 A1* | 11/2007 | Franer | A61B 17/3462 |
| | | | 604/167.02 |

FOREIGN PATENT DOCUMENTS

| | | |
|---|---|---|
| CN | 101474089 A | 7/2009 |
| CN | 101478924 A | 7/2009 |
| CN | 101480354 A | 7/2009 |
| CN | 202179583 U | 4/2012 |
| CN | 103505270 A | 1/2014 |
| CN | 203847533 U | 9/2014 |
| CN | 204351906 U | 5/2015 |
| CN | 204931836 U | 1/2016 |
| CN | 105443546 A | 3/2016 |
| CN | 205315435 U | 6/2016 |
| CN | 106108986 A | 11/2016 |
| EP | 0994740 A1 | 4/2000 |
| EP | 1759645 A1 | 3/2007 |
| WO | 8707928 A1 | 12/1987 |

\* cited by examiner

TROCAR SEAL MEMBRANE AND ASSEMBLY COMPRISING CONCAVE-CHANNELS

CROSS-REFERENCE TO RELATED APPLICATIONS

This application is a continuation of International Patent Application No. PCT/CN2017/093607 with a filing date of Jul. 20, 2017, designating the United States, now pending, and further claims priority to Chinese Patent Application No. 201610625833.6 with a filing date of Aug. 2, 2016. The content of the aforementioned applications, including any intervening amendments thereto, are incorporated herein by reference.

TECHNICAL FIELD

The present invention relates to a minimally invasive surgical instrument, and in particular, to a trocar sealing element.

BACKGROUND OF THE PRESENT INVENTION

A trocar is a surgical instrument, that is used to establish an artificial access in minimally invasive surgery (especially in rigid endoscopy). Trocars comprise in general a cannula and an obturator. The surgical use of trocars generally known as: first make the initial skin incision at the trocar insertion site, then insert the obturator into the cannula, and then together they facilitated penetration of the abdominal wall through incision into the body cavity. Once penetrated into the body cavity, the obturator is removed, and the cannula will be left as access for the instrument get in/out of the body cavity.

In rigid endoscopy surgery, it is usually necessary to establish and maintain a stable pneumoperitoneum for the sufficient surgical operation space. The cannula comprises a sleeve, an outer body, a seal membrane (also known as instrument seal) and a duck bill (also known as closure valve). Said cannula providing a channel for the instrumentation in/out of the body cavity, said outer body connecting the sleeve, the duck bill and the seal membrane into a sealing system; said, duck bill normally not providing sealing for the inserted instrument, but automatically closing and forming a seal when the instrument is removed; said seal membrane accomplishing a gas-tight seal against the instrument when it is inserted.

In a typical endoscopic procedure, it is usually set up 4 trocars (access), i.e. 2 sets of small diameter cannula (normally 5 mm in diameter), and 2 sets of large diameter cannula (normally 10~12 mm in diameter). Instruments, in general passing through a small cannula arc only for ancillary works; herein one large cannula as an endoscope channel, and the other large cannula as the main channel for surgeon to perform surgical procedures. Through said main channel thereof, 5 mm diameter instruments used in approximately 80% of the procedure, and said large cannula used in approximately 20% of the procedure; furthermore, 5 mm instruments and large diameter instruments need to be switched frequently. The small instruments are mostly used, so that the sealing reliability of which is more important. The large instruments are more preferably used in a critical stage of surgery (Such as vascular closure and tissue suturing), therein switching convenience and operational comfort are more important.

FIG. 1 and FIG. 2 depict a typical 12 mm diameter cannula 700. Said cannula 700 comprises a lower housing 710, an upper housing 720, a seal membrane 730 which sandwiched between the lower housing 710 and the upper housing 720, and a duckbill seal 750. Said lower housing 710 including center hole 713 defined by an elongated tube 711. Said upper housing 720 including the proximal hole 723 defined by the inner wall 721 Said membrane 730 including a proximal opening 732, a distal aperture 733, a sealing lip 734, a frustum sealing wall 735, a flange 736 and an outer floating portion 737. Said distal opening 733 formed by a sealing lip 734. Said sealing lip 734 defining a longitudinal axis 741, transverse plane 742 substantially perpendicular to said axis 741; define the angle between the rotary-generating line (or generatrix) of the frustum sealing wall 735 and the transverse plane 742 as a guide angle ANG1.

As illustrated in FIG. 1, when a 5 mm diameter instrument inserted, it is approximately considered that only hoop force generated by the deformation of the sealing lip 734, ensures a reliable seal for the instrument. It is nevertheless favorable to operate the instrument from various extreme angles in surgery. There's a lot space left for the 5 mm-instrument to move radially in the 12 mm diameter cannula, so that greater radial force would be taken by the sealing lip 734. Therefore, the sealing lip 734 should have sufficient hoop force for the inserted 5 mm diameter instrument to ensure its sealing reliability thereof.

As illustrated in FIG. 2, drawing a cylinder of Di (Di>5 mm) to cut the sealing wall 735 forms an intersecting line 738. It is easy to understand for those skilled in the art, when an Di diameter instrument is inserted, the strain (stress) of said sealing wall 735 in the area from the sealing lip 734 to the intersecting line 738 will be larger, so the area refer to as lip-adjacent area(or concentration stress area). While the strain (stress) of said sealing wall 735 from the intersecting, line 738 to the flange 736 is small. However, the different diameter (Di value) makes the boundary range of the lip-adjacent area (or concentration stress area) change larger or smaller. For the convenience of quantification, it is defined when Di is designed as the maximum diameter of the surgical instrument passing through the seal membrane, the area from the sealing lip 734 to the intersection line 738 is the lip-adjacent area.

As illustrated in FIG. 3, when a large diameter instrument is inserted (e.g. 12.8 mm), the sealing lip 734 will expand to a suitable size to accommodate the inserted instrument; said sealing wall 735 is divided into two portions: a conical wall 735c and a cylindrical wall 735d; said cylindrical wall 735d wrapped around the outer surface of the instrument to form a wrapped area with a high concentration of stress. Defining the intersecting line of the conical wall 735c and the cylindrical wall 735d as intersecting line 738a. When the instrument, is removed, said sealing wall 735 return to natural state, and said intersecting line 738a spring-back to a ring radius of Dx, defined as intersecting line 738b, (not shown in FIG); said intersecting line 738b is a bending boundary line when inserting a large diameter instrument. The angle between the rotary generating line of said conical wall 735c and the transverse plane 742 defines as ANG2, ANG2>ANG1; that is, when the large-diameter instrument is inserted, said sealing wall 735 rotates and stretch around its intersection line of said flange 736. Defining the height of the cylindrical wall 735d as Ha, not a fixed value; the factors such, as different size of said distal aperture, different size of said sealing lip, different thickness of said sealing wall, different said guide angle or different diameter of inserted instrument, make Ha different.

The instrument inserted into the sealing membrane and moved during surgical procedure, there is large frictional resistance between the wrapped area and the inserted instrument. Said large frictional resistance is normally easy to cause the seal inversion, poor comfort of performance, fatigue performance, even result in cannula insecurely fixed on the patient's abdominal wall etc., such that the performance of cannula assembly is affected.

Among the defects caused by the large frictional resistance, the seal inversion is one of the most serious problems that affecting the performance of the cannula. As illustrated in FIG. 4, when a large diameter instrument is removed, easily cause seal inversion. When inversion happened, said sealing wall 735 divided into a cylindrical wall 735e, a conical wall 735f, and a conical wall 735g; said cylindrical wall 735e wrapped around the outer surface of the instrument to form a wrapped area with a high concentration of stress. Defining the height of the cylindrical wall 735e to be Hb, normally Hb>Ha; that is, the frictional resistance when the instrument is removed greater than it when the instrument is inserted, this difference affects the surgeon's operating feeling and even make the surgeon confused. More seriously, the inversion of the seal membrane may stretch into the proximal hole 723, that is the seal membrane positioned between the instrument and the inner wail 721 gets completely jammed. Measures for preventing the seal inversion are respectively disclosed in U.S. Pat. Nos. 7,112,185 and 7,591,802, and those measures can effectively reduce the probability of inversion but not completely solve the problem.

The simplest way to reduce the frictional resistance is reducing the coefficient of friction between the two contacting surfaces with grease but the reliability of this way is not good. During procedures, due to instruments long-term repeated scraping with the seal membrane and repeated switching, it is easy to erase the grease off and carried away, resulting in bad lubrication.

A protector assembly adjoined by a seal membrane is disclosed in U.S. Pat. No. 5,342,315. Said protector to permit the sharp edge of the instrument to pass through the opening in the seal membrane without causing damage to the seal membrane, and the surface friction coefficient of the protector assembly is smaller than the surface friction coefficient of the seal membrane, which results in less frictional drag, but the lip-adjacent area is normally not completely covered by the protector assembly.

A seal member with ribs (or projections) is disclosed in U.S. Pat. No. 5,827,228, that is a plurality of spaced ribs provided to extend outwardly from center hole to reduce surface contact between the inserted instrument and the seal member, and thereby reducing the frictional resistance, a similar ribs which disclosed, in EP0994740 also reducing surface contact and strengthen the tensile of the seal member oriented to axial.

A sealing element comprising a flexible wall closed annularly with the edges foldable in a wave-like manner is disclosed in U.S. Pat. No. 7,842,014, wherein the wall bears a wave-like sealing lip and is a wavy pleated seal body, in such manner it can enlarge hoop circumference, and reduce the hoop force to a certain extent.

Chinese invention application CN101480354A (currently rejected) discloses a seal member containing an easily deformable groove, wherein is characterized in that it has a plurality of easily deformable grooves on the conical surface of the seal member from the sealing lip; said the thickness of the deformable groove wall is much smaller than the thickness of the conical surface wall, primary take advantage of the elongation of the deformable groove to accommodate the inserted large diameter instrument.

Although, in the prior art many solutions for reducing the frictional resistance have been disclosed, these solutions basically only propose measures from one certain factor affecting frictional resistance, the effect of which is small or not obvious. Some modifications solved a certain defects may lead to cause another bug. Such as, reinforcing ribs on the seal membrane to reduce surface contact, meanwhile strengthen the tensile of the seal membrane; or a deformable groove with a thickness much smaller than that of a truncated conical surface can cause the deformable groove to be easily damaged; due to the adoption of said wave-like sealing lip which enlarge hoop circumference, the sealing reliability will be sacrificed when a 5 mm diameter instrument is inserted, if the wave-like sealing lip is used but without enlarge hoop circumference, the wave-like sealing lip will lose its improvement effect. In summary there are many factors affecting the frictional resistance, and the comprehensive effects of various factors must be considered in the perspective of mechanics and tribology.

The seal membrane is preferably produced from rubber such as natural rubber, silicone or polyisoprene, its mechanical properties including super elastic and viscoelastic. Although the mechanical model of the rubber deformation process is complicated, it can still apply the generalized Hooke's law to describe approximatively its elastic behavior; and Newton's internal friction law to describe the viscous behavior. Research suggests that the main factors affecting the friction of the two surfaces in contact between the rubber and the instrument include: the smaller the friction coefficient of said two surfaces, the smaller the friction is; the better lubrication condition of said two surfaces in contact, the friction smaller is; the smaller normal pressure of said two surfaces, the friction smaller is. Comprehensively considering the above factors, the present invention proposes better solutions for reducing the frictional resistance between the seal membrane and the inserted instrument.

In addition to said frictional resistance greatly affecting the performance of the cannula assembly, the stick-slip of the seal membrane is another main factor affecting the performance of trocar. Said stick-slip means that when the instrument moves longitudinally in the sleeve, the sealing lip and lip-adjacent area sometimes are relatively statically attached to the instrument (at this point, the friction between the instrument and the seal membrane is mainly static friction.); but sometimes it produced a relatively slippery phenomenon with the instrument (at this point, the friction between the instrument and the seal membrane is mainly dynamic friction.); and said static friction is much greater than said dynamic friction. The two frictions alternately occur, which causes the movement resistance and speed of the instrument in the seal membrane to be unstable. It is easy to be understood for those skilled in the art, that in minimally invasive surgery the surgeon can only use surgical instruments to touch (feel) the patient's organs and observe a part of the working head of the instruments through endoscopic image system. In this case where the vision is limited and it cannot be touched, the surgeon typically uses the feedback of the resistance when moving instruments as one of the information to judge whether the operation is abnormal nor not. The stick-slip affects the comfort of operation, the accuracy of positioning, and even induces the surgeon to make false judgment.

During the surgical application of the cannula, the stick-slip is difficult to avoid, but can be reduced. Researches have shown that said stick-slip is affected by two main factors: one is that the smaller the difference between the maximum static friction and the dynamic friction, the weaker the stick-slip is; the other is that the larger the axial tensile stiffness of the seal membrane, the weaker the stick-slip is. Avoiding excessive the hoop force between the seal membrane and the instrument, reducing the two surfaces contacted, maintaining good lubrication, respectively, can reduce the difference between the maximum static friction and the dynamic friction, thereby reducing stick-slip, meanwhile, increasing the axial tensile stiffness of the seal membrane also helps to reduce the stick-slip phenomenon. The invention also proposes measures for improving stick-slip.

In summary, so far, there is no cannula that can effectively solve the said problems.

SUMMARY OF PRESENT INVENTION

In conclusion, one object of the invention is to provide a trocar seal membrane, said seal membrane comprises a proximal opening, a distal aperture, and a sealing wall from the distal aperture extending to the proximal opening, said distal aperture formed by a sealing lip for accommodating the inserted instrument and forming a gas-tight seal. Said the sealing wall includes a proximal surface and a distal surface. Said seal membrane can ensure a reliable seal for the inserted 5 mm instrument, and reduce frictional resistance and improve stick-slip when a large-diameter instrument is inserted.

As described in the background, the wrapped area formed by the sealing lip and the lip-adjacent area when a large diameter instrument inserted, is the major factor cause of frictional resistance. For reducing said frictional resistance, comprehensive consideration should be given such as reducing the radial stress between the instrument and the seal membrane, reducing said wrapped area, and reducing the actual contact area of the two surfaces. It is easy to understand for those skilled in the art that in accordance with the generalized Hooke's law and Poisson effect, enlarge hoop circumference, and reduce hoop strain (stress), thereby reducing radial strain (stress). But it should be noted that it is impossible to enlarging the hoop circumference in order to reduce the strain of the sealing lip which will result in reduced sealing reliability when applying 5 mm instruments. Since the stress in the lip-adjacent area is highly concentrated when applying a large diameter instrument, the hoop circumference of the lip-adjacent area should be rapidly increased. In regard to outside the lip-adjacent area, since the strain (stress) is small, it is not necessary to adopt measures to enlarge the hoop circumference. In addition, enlarging the hoop circumference, in the meantime increasing the axial tensile stiffness in the lip-adjacent area and maintain good lubrication (reducing difference between the maximum static friction and dynamic friction), thereby the stick-slip in the lip-adjacent area is improved.

In one aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal. Said sealing wall comprises the main rotary-wall and a plurality of concave-channels, which are recessed from the proximal surface of the main rotary-wall toward the distal surface and the concave-channels opening oriented to the proximal surface, and each of the concave-channels includes two side sealing-walls. Said concave-channels extend laterally outward from the sealing lip, and the depth of concave-channels gradually increases. Said sealing wall also includes a flange and a plurality of tilted sealing-walls extending from the flange and intersecting the side sealing-wall of said concave-channels. Said seal membrane also includes an outer floating bellows extending from the flange to the proximal opening with at least one radial (lateral) pleat.

In another aspect of the present invention, a seal membrane assembly includes an upper retainer ring, said seal membrane, a protection device and a lower retainer ring. Said upper retainer ring includes a proximal surface, a distal surface, an annular-shell extending from the distal surface to the proximal surface, and a plurality of cantilevers extending from said, annular-shell to the distal end. Said seal membrane and said protect device are sandwiched between the upper retainer ring and the lower retainer ring. Moreover, said cantilever are inserted into the concave-channel of said seal membrane and close to the tilted sealing-wall of said seal membrane.

In another aspect of the invention, an improved seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal. Said sealing wall comprises a main rotary-wall, a plurality of the first concave-channels and a plurality of the second concave-channels, and said first concave-channels and said second concave-channels are arranged alternately and are approximately evenly distributed around the sealing lip. Said first concave-channel or said second concave-channel is recessed from the proximal surface of the main rotary-wall toward the distal surface and the concave-channel opening oriented to the proximal surface, and each of the said concave-channel (said second concave-channel) includes two side sealing-walls. Said first concave-channel extends laterally outward from the sealing lip and gradually increase in its depth; said second concave-channel extends laterally outward from the sealing lip and gradually increases in its depth in the lip-adjacent area, while gradually decreases outside the lip-adjacent area. Said sealing wall also includes a flange and a plurality of tilted sealing-walls extending from the flange and intersecting the side sealing-wall of said first concave-channel.

In another aspect of the present invention, a seal membrane assembly includes the first retainer ring, the improved seal membrane, the second retainer ring, a protection device, a bellows and the third retainer ring. Said second retainer ring includes a proximal surface, a distal surface, an annular-shell extending from the distal surface to the proximal surface, and a plurality of cantilevers extending from said annular-shell to the distal end. Said seal membrane, second retainer ring, protect device and bellows are sequentially stacked all of which sandwiched between the first retainer ring and the third retainer ring. Moreover, the cantilever of the second retainer ring is inserted into the concave-channel of said seal membrane and close to the tilted sealing-wall of said seal membrane.

In another aspect of the invention, a trocar seal assembly comprises said seal membrane assembly, an upper body and an upper cover; the proximal opening of said seal membrane assembly is sandwiched between the upper body and the upper cover; said bellows makes said seal membrane assembly float laterally in the housing formed by the upper body and the cover.

It is believed that the above invention or other objects, features and advantages, will be understood with the drawings and detailed description.

DESCRIPTION OF THE DRAWINGS

A more complete appreciation of this invention, and many of the attendant advantages thereof will be readily apparent as the same becomes better understood by reference, to the following detailed description where.

In all views, the same referred number shows the same element or assembly.

DETAILED DESCRIPTION OF PREFERRED EMBODIMENTS

Embodiments of the invention are disclosed herein, however, it should be understood that the disclosed embodiments are merely examples of the invention, which may be implemented in different ways. Therefore, the invention is not intended to be limited to the detail shown, rather, it is only considered as the basis of the claims and the basis for teaching those skilled in the art how to use the invention.

Figures 1, 2:
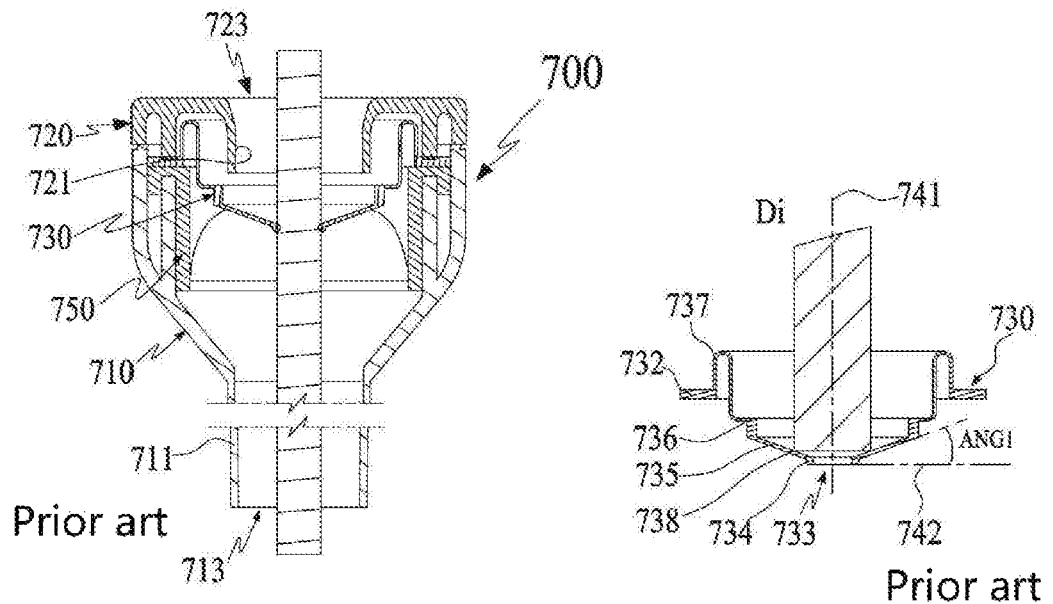
FIG. 1: shows a simulated distorted view of the cannula with the 5 mm diameter instrument inserted in the prior art.
FIG. 2: shows a detailed view of the seal membrane 730 in the prior art.
Figures 3, 4:
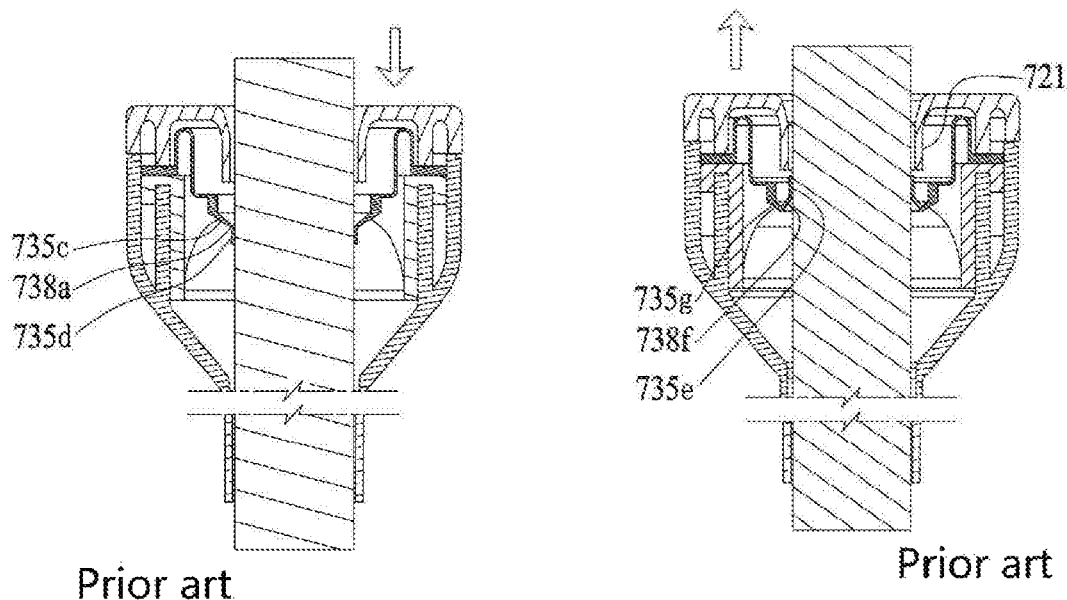
FIG. 3: shows a simulated distorted view of the cannula with the 12.8 mm diameter instrument inserted in the prior art.
FIG. 4: shows a simulated distorted view of the cannula with the 12.8 mm diameter instrument removed in the prior art.
Figure 5:
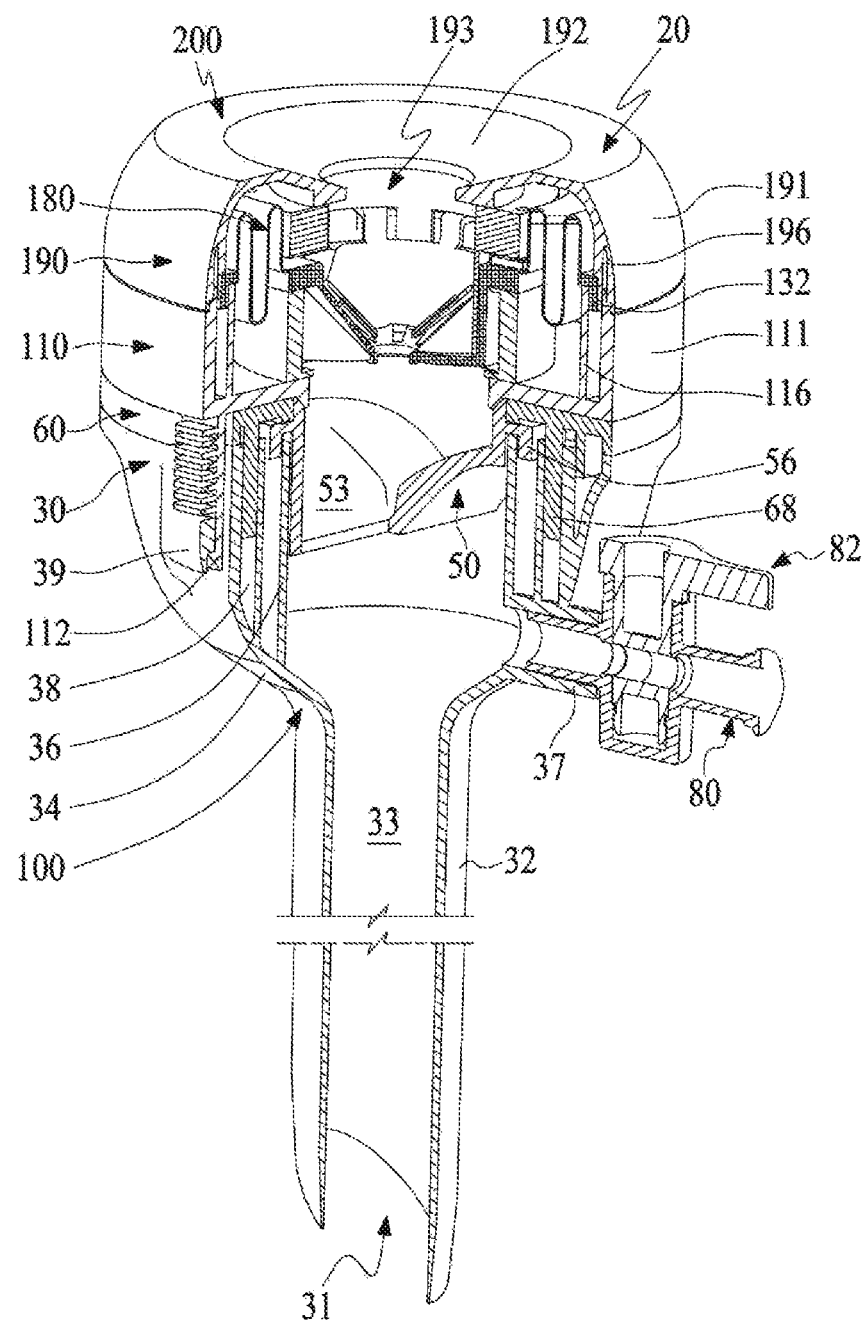
FIG. 5: shows a 3D perspective partial sectional view of the cannula in the invention.

FIG. 5 shows an overall view of the, structure of trocar. Atypical trocar comprises an obturator 10 (not shown) and a cannula 20. The cannula 20 comprises an open proximal end 192 and an open distal end 31. In a typical embodiment, said obturator 10 passes through said cannula 20, together they facilitated penetration of the abdominal wall through incision into the body cavity. Once penetrated into the body cavity, the obturator 10 is removed, and the cannula 20 will be left as access for the instrument get in/out of the body cavity. Said proximal end 192 in the external position of the patient and said distal end 31 in the internal position. A preferred cannula 20 can be divided into the first seal assembly 100 and the second seal assembly 200. Locking receptacle 39 in said seal assembly 100 can be locked with snap-in projection 112 in said seal assembly 200. The cooperation of snap-in projection 112 and the locking receptacle 39 can be quick release by one hand. The main purpose is for convenience of taking out tissues or foreign matter from the patient in the surgery. There are multiple ways to implement the quick release connection of said seal assembly 100 and assembly 200. In addition to the structure shown in this embodiment, a threaded connection, a rotary snap-in or other quick lock structure also may be applied. Alternatively, said assembly 100 and assembly 200 can be designed as a structure that can not be split quickly.

FIG. 5 shows the composition and assembly relationship of the first seal assembly 100. The lower body 30 includes an elongated tube 32, which defines the sleeve 33 passed through the distal end 31 and is connected to the outer housing 34. Said lower body 30 comprises an inner wall 36 supporting duck bill seal and a valve bore 37 that communicates with the inner wall 36. The plunger 82 mounted in the valve body 80, the said two are mounted into said valve bore 37. The flange 56 of the duck bill seal 50 is sandwiched between the inner wall 36 and the lower cover 60. There are various ways of fixing between the lower cover 60 and the lower body 30, such as the interference fit, ultrasonic welding, glue bonding, and snap fastening. 4 cylinders 68 of said lower cover 60, in this embodiment, 4 holes 38 of said lower body 30 are adopted to interference fit, so that the duckbill seal 50 is in the compressed state. Said tube 32, said the inner wall 36, said duck bill seal 50, said valve body 80 and said plunger 82 together are comprised the first chamber. Said duck bill seal 50, in this embodiment, is a single-slit, while other types of closure valves may also be used, including flapper valves, multi-silted duck bill valves. When the instrument is passed through said duck bill seal 50, the duckbill 53 will be opened, but it generally does not provide a complete seal against the instrument. When the instrument is removed, said duckbill 53 closed and substantially prevents insufflation fluid from escaping through the first chamber.

FIG. 5 shows the composition and assembly relationship of the second seal assembly 200. The seal membrane assembly 180 is sandwiched between the upper cover 110 and the upper body 190. The proximal end 132 of the seal membrane assembly 180 is secured between the inner ring 116 of the upper cover 110 and the inner ring 196 of the upper body 190. There are various secured ways between the upper, cover 190 and the upper body 110, such as the interference fit, ultrasonic welding, glue bonding, and snap fastening. The connection method, shown in this embodiment, is the outer shell 191 of the upper body 190 and the outer shell 111 of the upper cover 110 are secured by ultrasonic welding, so that the proximal end 132 of the seal membrane assembly 180 is in the compressed state. The center hole 113 of said upper cover 110, said inner ring 116, and said seal membrane assembly 180 together are comprised the second chamber.

Figure 6:
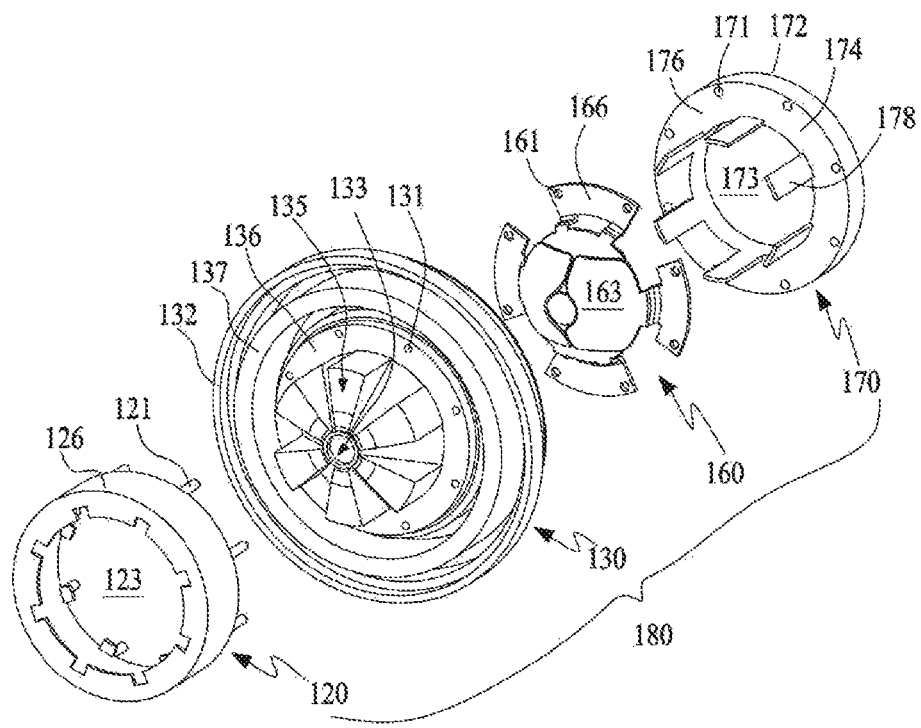
FIG. 6: shows an exploded view of the seal membrane assembly of the cannula in FIG. 5.
Figure 7:
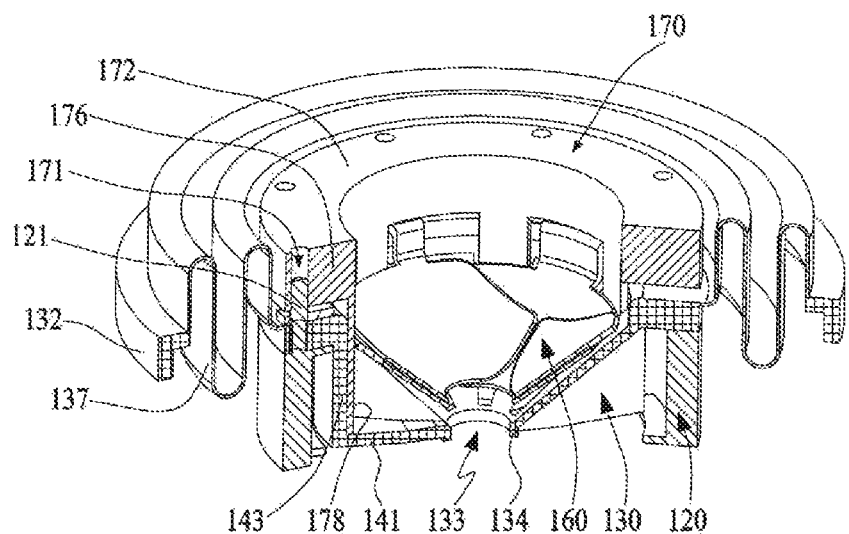
FIG. 7: shows a 3D perspective partial sectional view of the seal membrane assembly in FIG. 6.
Figure 8:
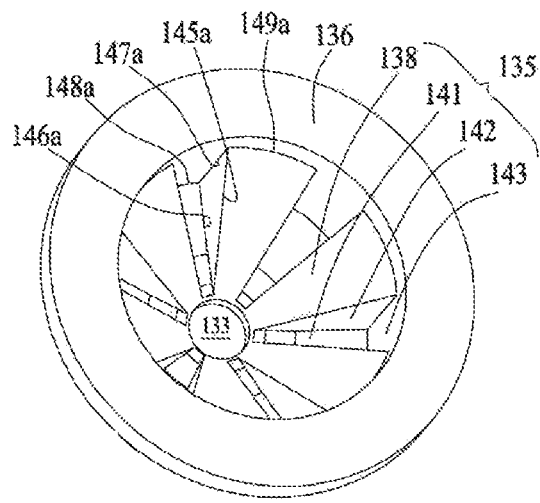
FIG. 8: shows a 3D perspective view of the seal membrane without the proximal end and floating portion in FIG. 6.
Figure 9:
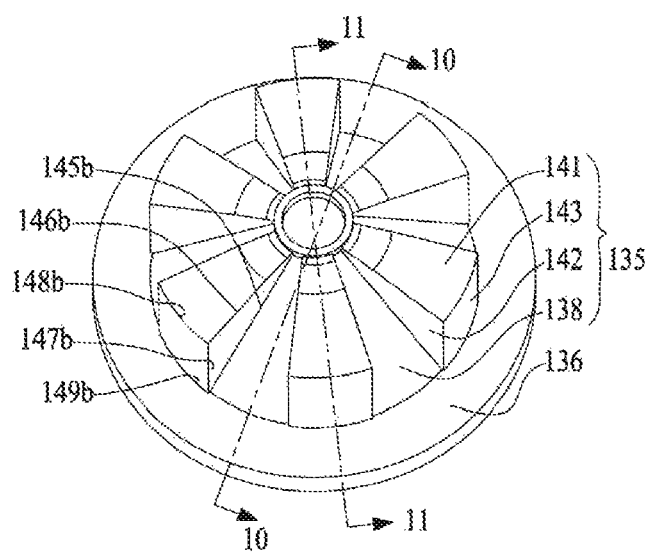
FIG. 9: shows a 3D perspective reserve view of the seal membrane in FIG. 8.
Figure 10:
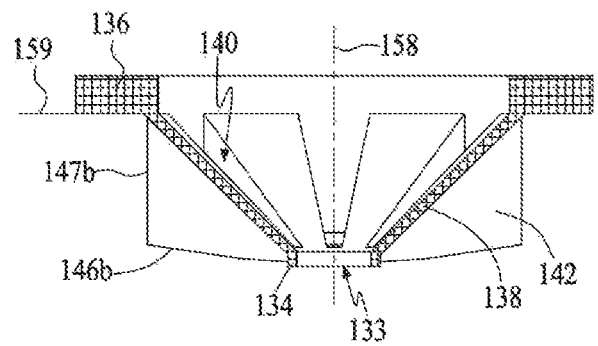
FIG. 10: shows a sectional view along line 10-10 in FIG. 9.
Figure 11:
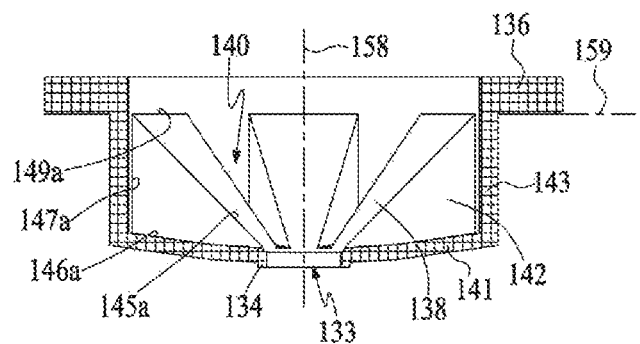
FIG. 11: shows a sectional view along line 11-11 in FIG. 9.

FIG. 6-7 illustrate the composition and assembly relationship of said seal membrane assembly 180, which including a lower retainer ring 120, a seal, membrane 130, a protection device 160 and an upper retainer ring 170. Said the seal membrane 130 and said protection device 170 are sandwiched between the lower retainer ring 120 and the upper retainer ring 125, moreover, the cylinder 121 of the said lower retainer ring 120 is aligned with corresponding holes on other components in said seal membrane assembly 180. Said cylinder 121 and the bore 171 of the upper retainer ring 170 are adopted to interference fit, so that the whole seal membrane assembly 180 is in the compressed state. Said protection device 160 includes 4 protectors 163 arranged so as to protect a center sealing body of said seal membrane 130, herein permit the sharp edge of the instrument to pass through without causing perforations or tears to the seal membrane 130.

Said seal membrane comprises a proximal opening 132, a distal aperture 133, and a sealing wall extending from the distal end to the proximal end, said sealing wall comprising a proximal surface and a distal surface. Said aperture 133 formed by a sealing lip 134 for accommodating an inserted instrument and forming a gas-tight seal. Said sealing lip 134, in the present embodiment, is approximately cylindrical, but said sealing lip 134 may be not circular.

Said the seal membrane 130 also includes the flange 136; the sealing wall 135 has one end connected to the sealing lip 134 and the other end connected to the flange 136; the floating portion 137 has one end connected to the flange 136 and the other end connected to said proximal end 132. Said flange 136 for mounting the protector device 160. Said floating portion 137 including one or several plurality of radial (lateral) pleats, so that the entire seal membrane assembly 180 can float in the assembly 200.

Said assembly 180 can be made from a variety of materials with a range of different properties. For instance, said seal membrane 130 is made of a super elastic material such as silicone or polyisoprene; said protector device 160 is made of a semi-rigid thermoplastic elastomer, and said second retainer ring 120 and said first retainer ring 170 are made of a relatively hard rigid material such as polycarbonate.

FIG. 8-11 show more detailed depiction of the seal membrane 130 in the first embodiment of the invention. In order to reduce the production cost, the seal membrane 130 is preferably designed as a monolithic part, but can also be designed as an inner seal body and an outer floating portion, separated from the flange 136. The first embodiment is mainly directed to the improvement of the inner seal body. To simplify the description, the outer floating portion and the proximal end are not shown in the subsequent description of the seal membrane. Defining a transverse plane 159 that is generally perpendicular to the longitudinal axis 158.

Said sealing wall 135, which can be approximately frustum, approximately hemispherical or an irregularly rotating surface. In this embodiment, said wall 135 is formed in an approximately conical arrangement surrounding the sealing lip 134. Said wall 135 including the main rotary-wall 138 and a plurality of concave-channels 140. Said concave-channels 140 are recessed from the proximal surface of the main rotary-wall 138, and the opening of concave-channel is towards the proximal surface. Said concave-channels 140 extend laterally outward from the sealing lip 134, and in the lip-adjacent area the depth of concave-channels gradually increases. Said a plurality of concave-channels 140 divided the main rotary-wall 138 approximately into a plurality of portions, that is said sealing wall 135 is a seamless sealing body formed by the main rotary-wall 138 and a plurality of concave-channels 140 arranged around the sealing lip 134 in an approximately conical manner.

Said concave-channel 140 includes a lower sealing-wall 141, a side sealing-wall 142 and a tilted sealing-wall 143. The first edge of said side sealing-wall 142 and said the main rotary-wall 138 formed an intersection line 145a, 145b; the second edge of said side sealing-wall 142 and said lower sealing-wall 141 formed an intersection line 146a,146b; the third edge of said side sealing-wall 142 and said tilted sealing-wall 143 formed an intersection line 147a,147b; said tilted sealing-wall 143 and said lower sealing-wall 141 formed an intersection line 148a, 148b; and said tilted sealing-wall 143 and said main rotary-wall 138 formed an intersection line 149a, 149b. Defining the angle between said intersection line 145a (145b) and said transverse plane surface 159 as α, which is called the guide angle, and 0°≤α<90° (when α is 0°, the rotary wall is parallel to the transverse plane, actually this can happen; When α is close to 90°, the main rotary-wall and the transverse plane are approximately vertical, in this case, the wrapped area is larger, when a large diameter instrument is inserted, normally the angle α should be <50°). The angle between said intersection line 145b and said intersection line 146b (or 145a and 146a) is defined as θ. The intersection of the two intersection lines (i.e. the apex of the angle θ) may be on the sealing lip 134; or the virtual extension lines of the two intersection lines intersect the inside of the, sealing lip 134. In the lip-adjacent area, the side sealing-wall 143 is a surface defined by both sides and extending laterally, outward from the sealing lip 134 and gradually widening.

Figure 12:
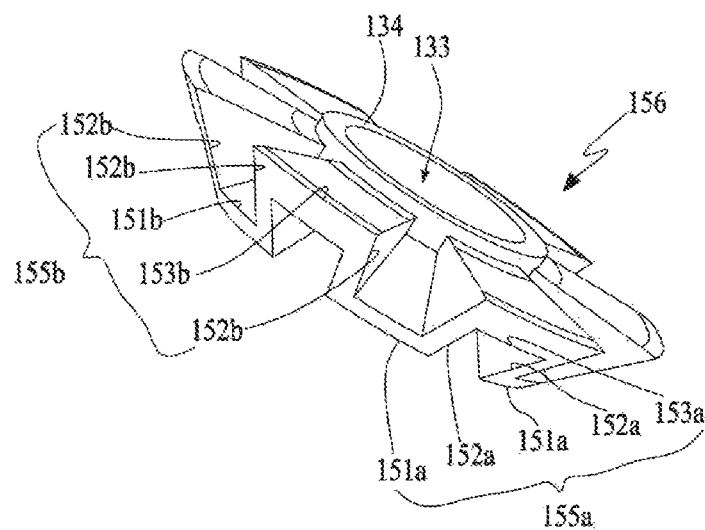
FIG. 12-13: shows a segmentation view of the seal membrane after the circumferential cutting separation in FIG. 9.
Figure 13:
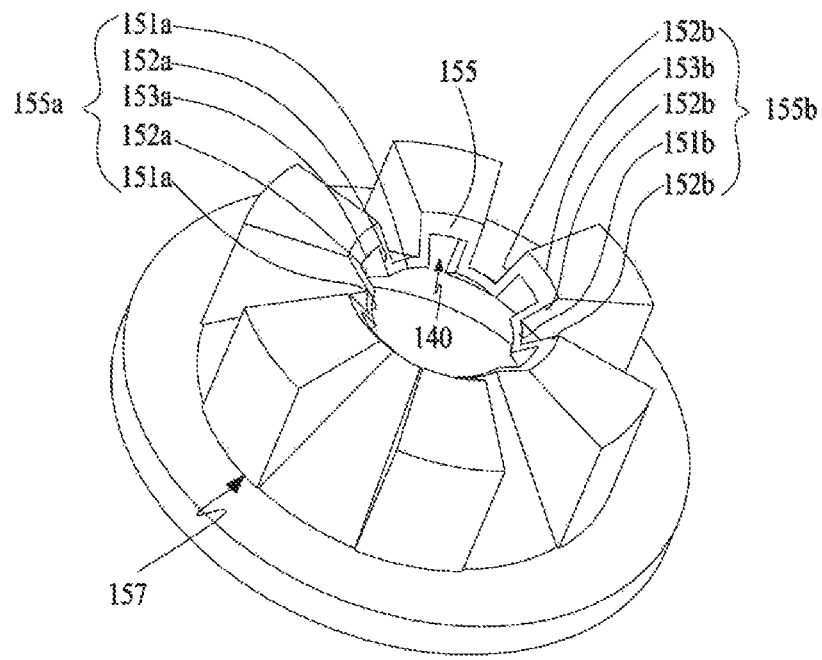

As FIG. 12-13 has shown, in an alternative embodiment, that the thickness of said sealing wall 135 is substantially uniform, that is, the thickness of the main rotary-wall 138, the lower sealing-wall 141 and the side sealing-wall 142 are substantially equal, so that the deformation of the sealing wall 135 is substantially uniform. However, the thickness of said substantially uniform wall should not be limited to the values of the absolute equality. When the number of said concave-channels is numerous, the thickness of the side sealing-wall 143 can be 0.05~0.25 mm thinner than the thickness of the lower sealing-wall 141 (or the side sealing-wall 142) for convenience of manufacture (for example, to enhance the strength of the mold at the concave-channel), or considering the tolerance. The thickness value of the lower sealing-wall 141, the side sealing-wall 142, and the tilted sealing-wall 143 is small, for convenience of quantification, the thickness ratio between the lower sealing-wall 141 (or tilted sealing-wall 143) and the side sealing-wall 142 said within 1~1.5, which still approximately consider that the thickness of the sealing wall 135 is substantially uniform and still does not deviate from the scope of the invention.

The sealing wall 135, in the present embodiment, comprises 6 linear concave-channels, however, a greater number or smaller of non-linear concave-channel may be adopted. The side sealing-wall 142 of the present embodiment is substantially parallel to the longitudinal axis 158, and in the lip-adjacent area, make a arbitrarily section plane that parallel to said axis 158 and meanwhile perpendicular to side sealing-walls 142, the intersected profile formed by said section plane and said concave-channels 140 is approximately U-shaped (the, intersected profiles of other concave-channels are also defined in this way). However, for convenience of manufacture, such as mold unloading, said side sealing-walls 142 may not be parallel to the longitudinal axis 158; that is, the section of the concave-channel 140 is approximately trapezoidal, even approximately V-shaped.

Taking the longitudinal axis 158 as a rotary axis, make a cylindrical surface with a radius R1 and intersects with said main rotary-wall 138 to form an intersection line, and create cutting plane M1 through said intersection line and perpendicular to the generating line of the main rotary-wall 138 (with the axis 158 as rotary axis). Said cutting plane M1 divides the seal membrane 130 into an inner portion 156 (as in FIG. 11) and an outer portion 157 (FIG. 12). Said cutting plane M1 intersects the main rotary-wall 138 to form a plurality of intersection lines 151a and 151b. Said cutting plane M1 intersects the side sealing-wall 142 to form a plurality of intersection lines 152a and 152b, and said cutting plane M1 intersects said lower sealing-wall 141 to form a plurality of intersection lines 153a and 153b. The plurality of segments 151a, 152a, 153a are formed an annular intersection line 155a; the plurality of segments 151b, 152b, 153b are formed an annular intersection line 155b, and the section 155 defined by said annular intersection line 155a and 155b.

As shown in FIG. 12-13, it is obvious that the circumference L1 of the intersection line 155a (155b) is much larger than $2*\pi*R1$, that means the concave-channel plays a role in enlarging hoop circumference, and the difference between L1 and $2*\pi*R1$ is approximately equal to $2*P$ times the length L2 of the intersection line 152a (152b) (P is the number of concave-channels). That is, the side sealing-wall 142 actually plays a role in enlarging hoop circumference. With the prerequisite of the concave-channels width meeting the needs of the manufacturer, enlarging the width of the concave-channel does not mean have a larger, hoop circumference.

Those skilled in the art can understand that there must be some R1 value making the outer portion 157, which is divided by the cutting plane M1, to start from the section 155, the main change of its shape is shown as local bending deformation and macroscopic displacement of the seal membrane, rather than the overall microscopic molecular chain elongation and overall tensile deformation. And said inner portion 156, from said sealing lip 134 to said section 155, the change of shape is shown as the comprehensive effect of partial bending deformation and overall tensile deformation of the seal membrane. What it is quite clear is that said concave-channels enlarge hoop circumference, and reduce the cylinder hoop strain (stress) when a large diameter instrument is inserted, thereby reducing the hoop force and the frictional resistance.

Referring to FIG. 6-7, said upper retainer ring 170 comprises a proximal surface 172, a distal surface 174, and an annular-shell 176 extending from the distal end to the proximal end, said annular-shell 176 defining the center hole 173. A plurality of through-holes 171 are substantially evenly distributed on the annular-shell 176, and a plurality of cantilevers 178 extend from said annular-shell to the distal end. Referring to FIG. 7, in said assembly 180, said cantilevers 178 is matched with the concave-channel 140, that is, the cantilever 178 is inserted into the concave-channel 140 and is close to or in contact with the tilted sealing-wall 143. And in the present embodiment, said tilted sealing-wall 143 is not in directly contact with the annular-shell of said lower retainer ring 120, with a sufficient clearance.

Figure 14:
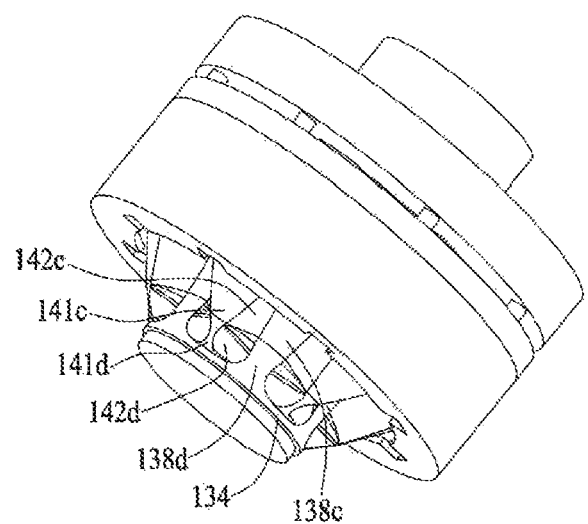
FIG. 14: shows a simulated distorted view of the seal membrane with the 12.8 mm instrument inserted in FIG. 7.
Figure 15:
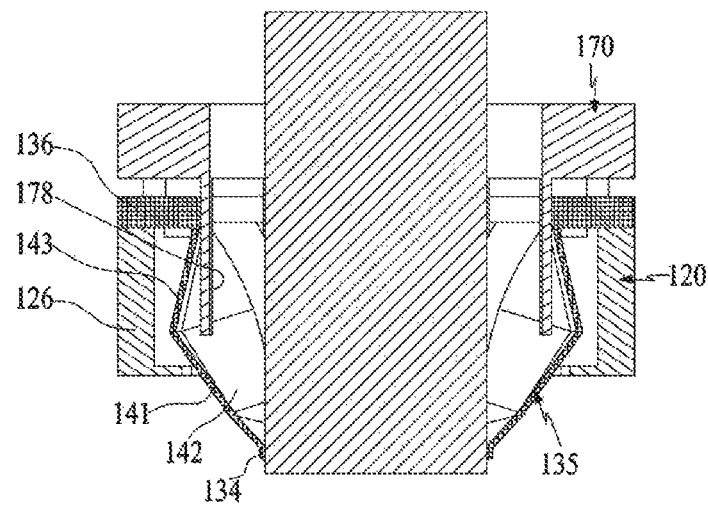
FIG. 15: shows a simulated distorted longitudinal view illustrated in FIG. 14.
Figure 16:
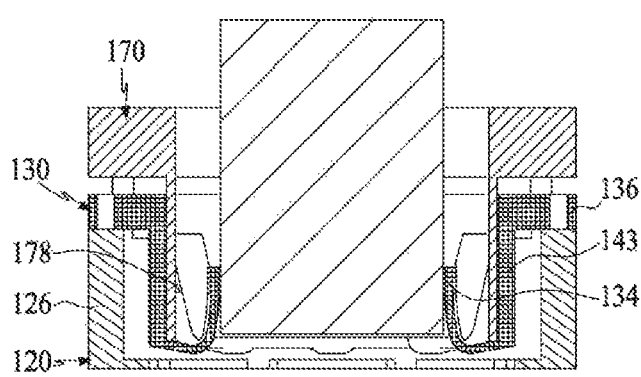
FIG. 16: shows a simulated distorted view of the seal membrane assembly with the 12.8 mm instrument removed in FIG. 14.
Figure 17:
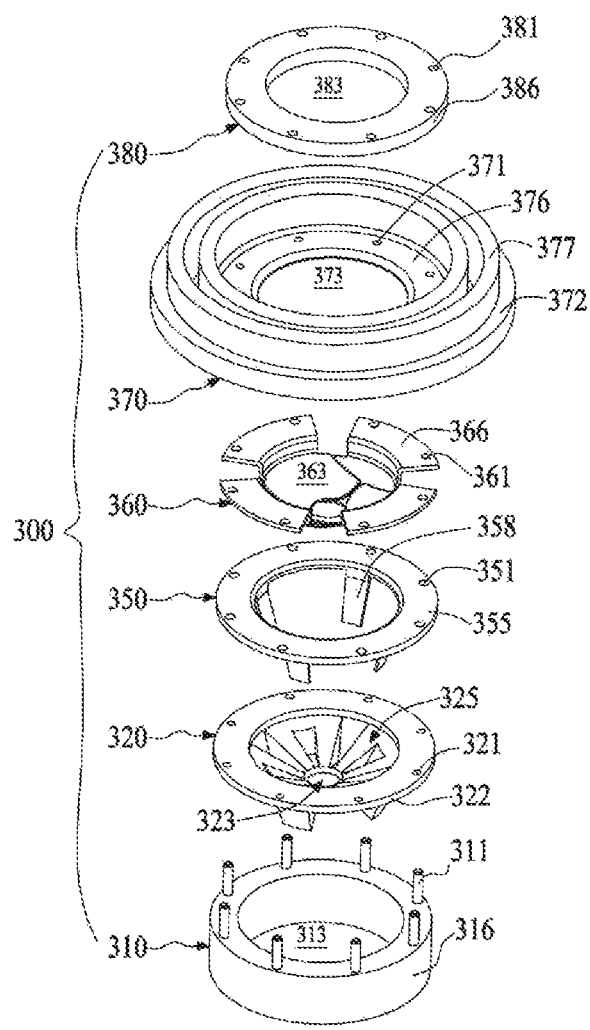
FIG. 17: shows an exploded view of the seal membrane assembly in the second embodiment.

FIG. 14-16 shows a simulated deformation view of the seal membrane 130 when a large diameter instrument is inserted into said seal membrane assembly 180 (the floating portion outside the seal membrane and the protect device 160 are not shown). Said lower sealing-wall 141 is divided into two portions, a lower sealing-wall 141c and a cylindrical wall 141d; while said a side sealing-wall 142 is divided into two portions, a side sealing-wall 142c and a cylindrical wall 142d; said the main rotary-wall 138 is divided into two portions, a main rotary-wall 138c and a cylindrical wall 138d. Said cylindrical wall 141d, said cylindrical wall 142d, and said cylindrical wall 138d together forms the wrapped area around the outer surface of said inserted instrument. Studies have shown that, compared to the grooveless design, the wrapped area of the, sealing body with the concave-channel is small, and reducing the wrapped area can reduce the frictional resistance.

In the present embodiment, the structure of said concave-channels enlarges hoop circumference, and said side sealing-wall 142 increases local bending stiffness of the sealing wall 135. Referring to FIG. 15 Said scaling lip 134 is stretched enough to accommodate the inserted instrument, the sealing wall 135 rotates and stretches outwardly around, its intersection part with the flange 136; and said side sealing-wall 142 forces the tilted sealing-wall 143 to rotate and stretch outwardly around its intersection part with the flange 136 too. In the present embodiment, a sufficient gap is reserved between said tilted sealing-wall and said annular-shell, so said sealing wall 35 is free to be stretched, and deformed outwardly, and there is no (or very small) extrusion force between the tilted sealing-wall 143 and the annular-shell, thereby reducing the normal pressure of said two surfaces in contact between the wrapped area and the instrument.

Referring to FIG. 16, when the large diameter instrument is removed out from the seal membrane assembly 180, the seal membrane may be inverted under certain circumstance. In the present embodiment said cantilever 178 blocks the inversion path of the tilted sealing-wall 143; The lower sealing-wall 141 is connected to the tilted sealing-wall 143, the tilted sealing-wall 143 pulling the lower sealing-wall 141 and the lower sealing-wall 141 pulling the sealing lip 134, thereby limiting the depth of the seal inversion, only locally and partially inversion; effectively reducing the wrapped area after the inversion. Therefore, the operational comfort of the seal membrane after inversion can be improved to a large extent.

In the present embodiment, the side sealing-walls 142 together reinforce the axial tensile stiffness in the lip-adjacent area; and said side sealing-wall 142 increases the axial tensile stiffness without increasing the hoop stiffness, thus increasing the axial stiffness without increasing the hoop force, such that which can effectively reduce the stick-slip described in the background. In the embodiment, 12 side sealing-walls 142 are included, while more or less side sealing-walls also reinforce the axial tensile stiffness.

The concave-channel 140 can be used to store grease. As FIG. 14-15 have shown, when a large diameter instrument is inserted, the wrapped area deformed by said concave-channel is smaller, only a small section of the concave-channel 140 is flattened. The unflattened concave-channel near the wrapped area has a better function of storing grease. When the instrument moves in the seal membrane, the grease in the wrapped area is scraped away firstly, and the grease in the unflattened concave-channel adjacent to the wrapped area will be added to the surface of the instrument, thereby adding grease to the wrapped area with the instrument moving. Optionally, the internal width of the concave-channel in the lip-adjacent area is B1, wherein 0.5 mm≤B1≤1 mm. When the inner width of the concave-channel in the lip-adjacent area is smaller than 0.5 mm, the structure of the concave-channel is hard to be manufactured; while the larger the internal width of the concave-channel, the worse the grease storage effect; Researches have shown that when the internal width of the groove is ≤1 mm, the grease storage effect is better. The grease storage of the grooves improves the problem of lubrication unreliability as described in the background, thereby contributing to reduce the stick-slip described in the background.

In summary, the structure of concave-channels has the functions of enlarging hoop circumference, reducing the wrapped area, reducing the actual contact area of the two surfaces between the instrument and the seal membrane, improving lubrication reliability, increasing the axial tensile stiffness, etc., thereby, the frictional resistance and the stick-slip can, be greatly reduced, and the probability of inversion is reduced and the comfort of application is improved.

FIG. 17-23 show more detailed depiction the seal membrane assembly 300 of the second embodiment of the invention. Said seal membrane assembly 300 includes the third retainer ring 310, a seal membrane 320, the second retainer ring 350, a protection device 360, a bellows 370 and the first retainer ring 380. Said seal membrane 320, the second retainer ring 350, protect device 360 and bellows 370 are sequentially stacked, all of which sandwiched between the first retainer ring 380 and the third retainer ring 310; the cylinder 311 of the third retainer ring 310 is aligned with corresponding, holes on other components in said assembly 300; the cylinder 311 and the first retainer ring 380 are adopted to interference fit so that the whole seal membrane assembly 300 is in the compressed state. Said protection device 360 includes 4 protectors 363 arranged so as to protect a center sealing body of said seal membrane 330, herein permit the sharp edge of the instrument to pass through without causing perforations or tears. Said bellows includes a flange 376, transverse pleats 377, a proximal end 372 and a plurality of through-holes 371 substantially evenly distributed on the annular wall 376. When the seal membrane assembly 300 is replaced with the seal membrane assembly 180 in the aforementioned second seal assembly 200, said bellows 370 allows the entire seal membrane assembly 300 floating in the second seal assembly 200.

Figure 18:
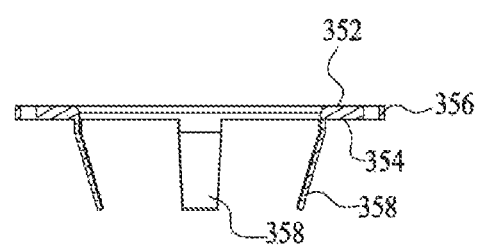
FIG. 18: shows a longitudinal view of the second retainer ring in the seal membrane assembly illustrated in FIG. 17.
Figure 19:
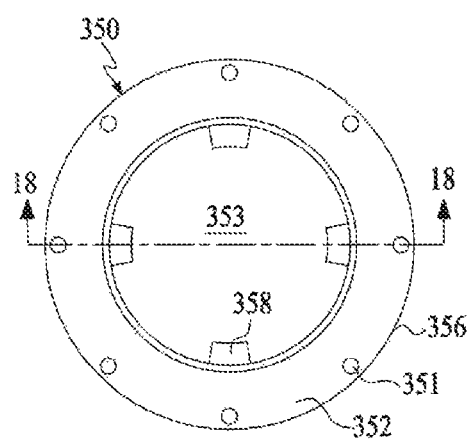
FIG. 19: shows a plane projection view of the second retainer ring in the seal membrane assembly illustrated, in FIG. 17.
Figure 20:
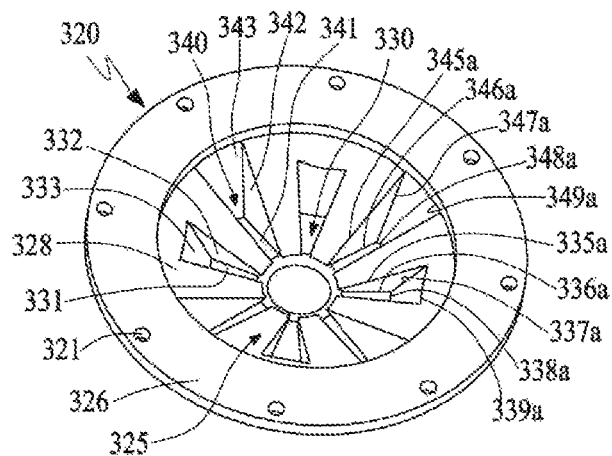
FIG. 20: shows a 3D perspective view of the seal membrane in the seal membrane assembly illustrated in FIG. 17.

FIG. 18-19 depict the structure of the second retainer ring 350 in more detail. Said second retainer ring 350 comprises a proximal surface 352, a distal surface 354, and an annular-shell 356 extending from the distal end to the proximal end; a plurality of through-holes 351 are substantially evenly distributed on the annular-shell 356, and a plurality of cantilevers 358 extend from said annular-shell 356 to the distal end.

Figure 21:
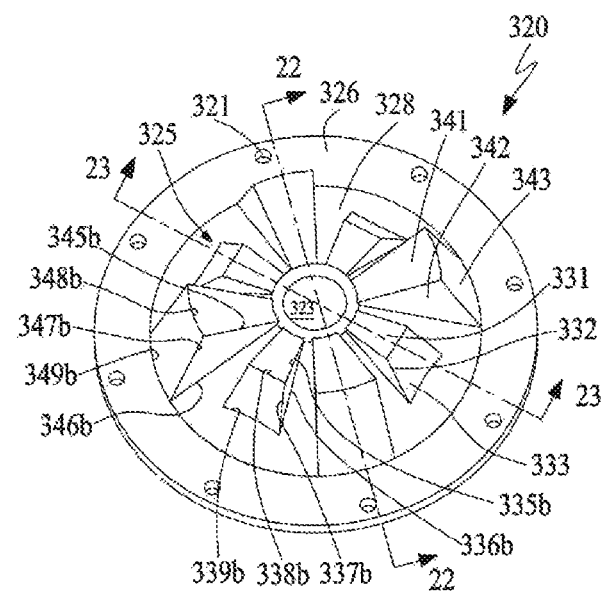
FIG. 21: shows a 3D perspective reserve view of the seal membrane in FIG. 20.
Figure 22:
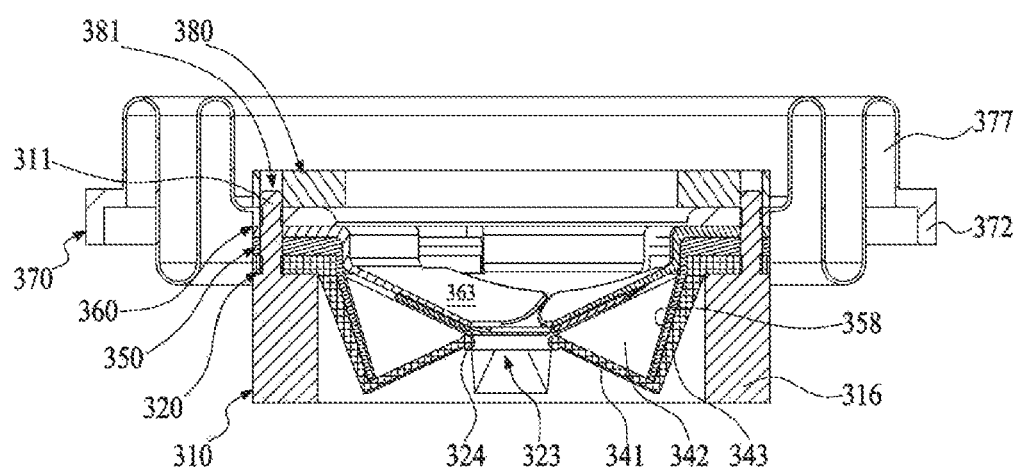
FIG. 22: shows a sectional view of the seal membrane assembly in FIG. 17 and along line 22-22 in FIG. 21.
Figure 23:
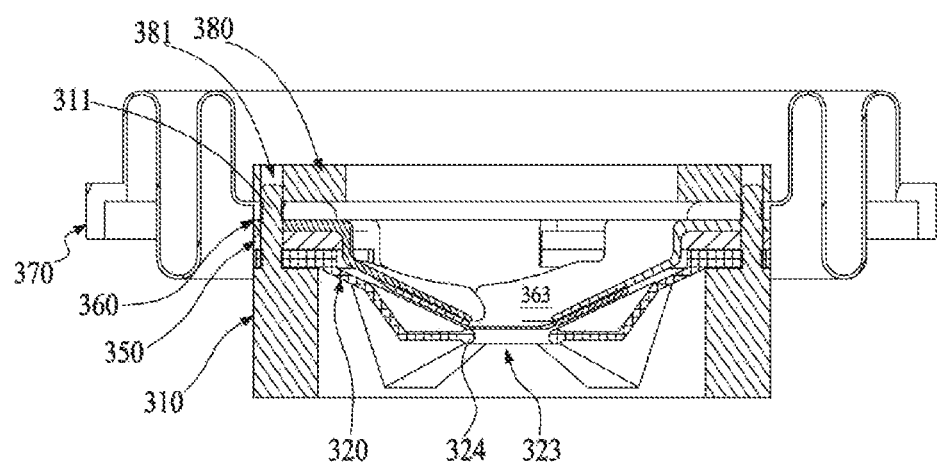
FIG. 23: shows a sectional view of the seal membrane assembly in FIG. 17 and along line 23-23 in FIG. 21.

FIG. 21-23 depict the seal membrane 320 and the seal membrane assembly 300 in more detail. Said the seal membrane 320 comprises a distal aperture 323, a sealing lip 324, a sealing wall 325 and a flange 326. Said distal aperture 323 formed by the sealing lip 324, said sealing wall 325 connecting the sealing lip 324 at one end and the flange 326 at the other end, said seal membrane including the proximal surface and the distal surface. Defining the axis of said sealing lip 324 as the longitudinal axis 358, and a transverse plane 359 that is generally perpendicular to the longitudinal axis 358.

Said wall 325 including the main rotary-wall 340, a plurality of the first concave-channels 340 and a plurality of second concave-channels 330. The second concave-channels 330 and the first concave-channels 340 extend laterally outward from the sealing lip 324. The openings of the second concave-channels 330 and the first concave-channels 340 oriented to the proximal surface. A plurality of the second concave-channels 330 and the plurality of first concave-channels 340 are alternately arranged on the main rotary-wall 328, which is approximately equally divided into a plurality of portions. That is said sealing wall 335 is a seamless sealing body formed by the main rotary-wall 338 and a plurality of the second concave-channels 330, the first concave-channels 340 arranged around the sealing lip 324 in an approximately conical manner. The sealing wall 335, in the present embodiment, comprises 4 linear second concave-channels 330 and 4 linear first concave-channels 340, however, a greater or a smaller number of non-linear concave-channel may be adopted. The section of said concave-channels is approximately U-shaped.

Said second concave-channel 330 includes a lower sealing-wall 331, a side sealing-wall 332 and a tilted sealing-wall 333. The first edge of said side sealing-wall 332 and said the main rotary-wall 328 formed an intersection line 335a, 335b; the second edge of said side sealing-wall 332 and said lower sealing-wall 331 formed an intersection line 336a, 336b; the third edge of said side sealing-wall 332 and said tilted sealing-wall 333 formed an intersection line 337a, 337b; said tilted sealing-wall 333 and said lower sealing-wall 331 formed an intersection line 338, 338b; and said tilted sealing-wall 333 and said main rotary-wall 328 formed an intersection line 339a, 339b; the depth of said second concave-channel 330 gradually increases in the lip-adjacent area along longitudinal axis, and the depth of which rapidly decreases outside the lip-adjacent area. The measurement method of the concave-channel depth is: the shortest distance from the point at the bottom of the concave-channel recessed to the main rotary-wall along longitudinal axis.

Said first concave-channel 340 includes a lower sealing-wall 341, a side sealing-wall 342 and a tilted sealing-wall 343. The first edge of said side sealing-wall 342 and said the main rotary-wall 328 formed an intersection line 345a, 345b; the second edge of said side sealing-wall 342 and said lower sealing-wall 331 formed an intersection line 346a, 346b; the third edge of said side sealing-wall 342 and said tilted sealing-wail 343 formed an intersection line 347a, 347b; said tilted sealing-wall 343 and said lower sealing-wall 331 formed an intersection line 348a, 348b; said tilted sealing-wall 343 and said main rotary-wall 328 formed an intersection, line 349a, 349b; the depth of said first concave-channel 340 gradually increases in the lip-adjacent area along longitudinal axis, and the depth of which rapidly decreases outside the lip-adjacent area. The tilted sealing-wall 343 is a part of a conical wall or a cylindrical wall. The shape and structure of the first concave-channel 340 and the second concave-channel 330 may be the same or different: the length of the first concave-channel 340 is longer than the second concave-channel 330.

Referring to FIG. 22-23, the cantilever 358 of the second retainer ring 350 matches the first concave-channel 340. That is, the cantilever 358 is inserted into the first concave-channel 340, and is close to or in contact with the tilted sealing-wall 343. As described above, when a large diameter instrument is inserted into the seal membrane assembly 300, said sealing wall 325 is free to be stretched and deformed outwardly, and there is no (or very small) extrusion force between the tilted sealing-wall 343 and the third retainer ring 310. Thereby reducing the normal pressure of said two surfaces in contact between the wrapped area and the instrument. When the large diameter instrument is removed out from the seal membrane assembly 300, the seal membrane may be inverted under certain circumstance. In the present embodiment said cantilever 358 blocks the inversion path of the tilted sealing-wall 343: the lower sealing-wall 341 is connected to the tilted sealing-wall 343, the tilted sealing-wall 343 stretches the lower sealing-wall 341 and the lower sealing-wall 341 stretches the sealing lip 324, thereby limiting the depth of the seal inversion, only local inversion; effectively reducing the wrapped area after the inversion. Moreover, said the length of the second concave-channel 330 is smaller than the first concave-channel 340, which helps to reduce the actual contact area of the two surfaces between the seal membrane and the instrument after inversion; thereby improving the operational comfort after the seal inversion to a large extent.

Those skilled in the art easily understand that the reasonable fillet transition can avoid stress concentration or make certain areas deformed more easily. Due to the small size of the seal membrane, especially the area near the sealing lip is smaller, with such a small size and different chamfer, the shape of the seal membrane looks different. In order to clearly show the geometric relationship of the elements, the embodiment of the invention is generally the pattern without the fillet.

Many different embodiments and examples of the invention have been shown and described. One of those ordinary skilled in the art will be able to make adaptations to the methods and apparatus by appropriate modifications without departing from the scope of the invention. The approximate U-shaped concave-channels and the approximate V-shaped concave-channels described in this embodiment cannot be limited to U-shaped or V-shaped. It has been mentioned many times in the invention that the concave-channel extends laterally outward from the sealing lip, and the so-called "extending laterally outward" should not be limited to a straight line. Said "extending laterally outward" can be a spiral, a line segment, a multi-section arc line and so on. In the invention, the positional relationship of the intersecting surfaces composed of said concave-channel and the intersection line thereof are described with reference to specific embodiments, and the methods of increasing curved surfaces to form a multifaceted mosaic or using of the high-order curved surface to make the intersection line and the concave-channel shape to look different from said embodiment. However, it can be considered not deviated from the scope of the invention, as long as it conforms to the general idea of the invention. Several modifications have been mentioned, to those skilled in the art, other modifications are also conceivable. Therefore, the scope of the invention should follow the additional claims, and at the same time, it should not be understood that it is limited by the specification of the structure, material or behavior illustrated and documented in the description and drawings.

I claim:

1. The concave-channels extend laterally outward from the sealing lip, and a depth of the concave-channels gradually increases; and the upper retainer ring includes a proximal surface, a distal surface, an annular-shell extending from the distal surface to the proximal surface, and a plurality of cantilevers extending from the annular-shell to the distal end; the seal membrane and the protection device are sandwiched between the upper retainer ring and the lower retainer ring; the cantilevers are inserted into and matched with the concave-channels and close to the tilted sealing-walls of the seal membrane.

2. The seal membrane assembly of claim 1, when a large diameter surgical instrument is inserted into the trocar, the side sealing-walls increase an axial tensile stiffness, and an actual contact area of two surfaces between the instrument and the seal membrane and a wrapped area are reduced.

3. The seal membrane assembly of claim 1, when the large diameter instrument is removed out from the seal membrane assembly, the cantilevers block an inversion path of the sealing-wall, limit the depth of the seal inversion, and reduce the wrapped area after the inversion.

4. The seal membrane assembly of claim 1, an internal width of the concave-channel in the lip-adjacent area is B and $0.5 \leq B \leq 1$ millimeter.

5. The seal membrane assembly of claim 4, wherein the seal assembly also includes a lubricating grease; the concave-channel stores grease; when a large diameter surgical instrument is inserted into the trocar, a small, section of the concave-channel is flattened and the other section of the concave-channel is unflattened.

6. A trocar seal membrane assembly comprising a seal membrane; the seal membrane comprises, a proximal opening, a distal aperture, and a sealing wall extending from the distal aperture to the proximal opening; the sealing wall comprises a proximal surface and a distal surface; the distal aperture is formed by a sealing lip for accommodating an inserted instrument and forming a gas-tight seal;

the sealing wall comprises a main rotary-wall and a plurality of concave-channels; the plurality of the concave-channels are recessed from the proximal surface of the main rotary-wall to the distal surface of the main rotary-wall; openings of the concave-channels are oriented to the proximal surfaces; the main rotary-wall is divided into a plurality of portions by the concave-channels; and each of the concave-channels includes two side sealing-walls and one lower sealing-wall;

the concave-channels extend laterally outward from the sealing lip, and a depth of the concave-channels gradually increases; and the sealing wall also includes a flange and a plurality of tilted sealing-walls extending from the flange and intersecting the side sealing-wall of the concave-channels;

wherein the concave-channels comprise first concave-channels and second concave-channels; the first concave-channels and the second concave-channels extend laterally outward from the sealing lip; and the depth of the second concave-channels gradually increases in the lip-adjacent area along the a longitudinal axis of the distal aperture, the depth of the second concave-channels decreases outside the lip-adjacent area; the depth of the first concave-channel gradually increases in the lip-adjacent area; the depth of the first concave- channel gradually decreases far-away from the lip-adjacent area;

the first concave-channels and the second concave-channels are alternately arranged around the sealing lip; and the sealing wall also includes a second plurality of tilted sealing-walls extending from the flange and intersecting the side sealing-wall of the second concave-channels;

wherein the seal assembly further comprises a first retainer ring, a second retainer ring, a protection device, a third retainer ring and a bellow; the second retainer ring includes a proximal surface, a distal surface, an annular-shell extending from the distal surface to the proximal surface, and a plurality of cantilevers extending from the annular-shell to the distal end; and the seal membrane, the second retainer ring, the protection device and the bellow are sequentially stacked and sandwiched between the first retainer ring and the third retainer ring;

and the cantilevers are inserted into and matched with the first concave-channels and are arranged close to the tilted sealing-walls of the seal membrane.

\* \* \* \* \*